United States Patent [19]

Smith et al.

[11] 4,169,013

[45] Sep. 25, 1979

[54] PROCESS FOR PREPARING GLUCOAMYLASE

[75] Inventors: Jay A. Smith, Downers Grove; Jeffrey R. Frankiewicz, Lombard, both of Ill.

[73] Assignee: CPC International Inc., Englewood Cliffs, N.J.

[21] Appl. No.: 709,148

[22] Filed: Jul. 28, 1976

Related U.S. Application Data

[63] Continuation of Ser. No. 529,879, Dec. 5, 1974, abandoned.

[51] Int. Cl.$^2$ .............................................. C12N 9/34
[52] U.S. Cl. .................................. 435/205; 435/254; 435/917
[58] Field of Search .................... 195/66 R, 62, 31 R, 195/100, 102, 101, 65, 83, 88; 426/7, 11, 12

[56] References Cited

U.S. PATENT DOCUMENTS

| | | | |
|---|---|---|---|
| 2,881,115 | 4/1959 | Liggett et al. | 195/66 R |
| 3,249,512 | 5/1966 | Bode | 195/31 R |
| 3,418,211 | 12/1968 | Van Lanen et al. | 195/31 R |
| 3,677,902 | 7/1972 | Aunstrup | 195/66 R |
| 3,720,583 | 3/1973 | Fisher | 195/31 R |
| 3,912,590 | 10/1975 | Slott et al. | 195/31 R |
| 3,922,197 | 11/1975 | Leach et al. | 195/31 R |

FOREIGN PATENT DOCUMENTS 2025748  12/1970  Fed. Rep. of Germany ........ 195/66 R

OTHER PUBLICATIONS

Madsen, et al., "A New Heat Stable Bacterial Amylase and its Use in High Temperature Liquefaction", *Die Stärke*, vol. 25, No. 9, pp. 304–308, (1973).

*Primary Examiner*—Thomas G. Wiseman

[57] ABSTRACT

Glucoamylase is prepared by fermenting a microorganism capable of producing glucoamylase in a nutrient medium containing at least about 16% to about 25% of ground corn which has been liquefied by the action of heat, water and an alpha-amylase enzyme preparation. The alpha-amylase enzyme preparation is preferably derived from a microorganism of *Bacillus licheniformis*.

8 Claims, No Drawings

PROCESS FOR PREPARING GLUCOAMYLASE

This is a continuation of copending application Ser. No. 529,879, filed Dec. 5, 1974, now abandoned.

BACKGROUND OF THE INVENTION

1. Field of the Invention

This invention relates to the production of glucoamylase. This invention is also concerned with improving the yield during the fermentation process in the production of glucoamylase.

2. Description Of The Prior Art

Glucoamylase is an enzyme capable of converting starch to dextrose. The use of glucoamylase for producing dextrose and dextrose-containing syrups is well known in the art. Processes using glucoamylase generally fall into three categories. These are the acid-liquefaction-enzyme conversion process, the enzyme-liquefaction-enzyme conversion process, and the enzyme solubilization-enzyme conversion process (the granular starch hydrolysis process as disclosed and claimed in U.S. Ser. Nos. 437,101; 437,264; and 437,452, filed Jan. 28, 1974, and Ser. No. 452,154, filed Mar. 18, 1974, now U.S. Pat. Nos. 3,922,197; 3,922,198; 3,922,199; and 3,922,200, respectively, granted Nov. 25, 1975).

In the acid-enzyme process, starch is liquefied and hydrolyzed in an aqueous suspension containing 20 to 40 percent starch and an acid, such as hydrochloric acid. The suspension is then heated to a high temperature, i.e., a temperature between about 70° C. and about 160° C. and at a pH between about 1 and 4.5 to liquefy and partially hydrolyze the starch. The liquefied and partially solubilized starch will generally have a dextrose equivalent value (D.E.) up to about 20 and preferably up to about 15. Typical acid-enzyme processes are disclosed in U.S. Pat. Nos. 2,305,168; 2,531,999; 2,893,921; 3,042,584 and 3,012,944.

In the enzyme-enzyme process, starch is liquefied and hydrolyzed in an aqueous suspension containing 20 to 40 percent starch and a liquefying enzyme such as bacterial alpha-amylase enzyme at a temperature of from about 85° C. to about 105° C. The dextrose equivalent value of the liquefied and partially hydrolyzed starch is generally less than about 20 and preferably less than about 15. A revolutionary process for preparing a partial hydrolyzates suitable for converting starch to dextrose and dextrose-containing syrups comprises liquefying starch in water with a bacterial alpha-amylase enzyme preparation to a dextrose equivalent value of from about 2 to about 15, heat treating the slurry containing the liquefied starch to a temperature greater than about 95° C., and thereafter converting the liquefied starch with a bacterial alpha-amylase enzyme preparation to a D.E. of up to about 20. This revolutionary process is disclosed and claimed in U.S. Ser. No. 107,436, U.S. Pat. No. 3,853,706.

In the enzyme-enzyme granular starch process, a slurry of granular starch is solubilized by the action of bacterial alpha-amylase (preferably a bacterial alpha-amylase enzyme preparation derived from the microorganism *Bacillus licheniformis*) under conditions such that the starch is not gelatinized or thinned. The solubilized starch may be thereafter converted to dextrose or dextrose-containing syrups by other enzymes such as glucoamylase.

The partially hydrolysed or solubilized starch products prepared by any one of the three processes mentioned above may then be treated with glucoamylase enzyme preparations to convert the starch hydrolysate to dextrose or dextrose-containing syrups.

The enzymatically converted hydrolysates are then subjected to known carbon and ion exchange refining processes to remove color bodies, odoriferous materials, and constituents which contribute to the ash content of the hydrolysates. Such known treatments involve treating the syrup with activated carbon at an acidic pH (i.e., a pH of about 4 to 6, the pH activated carbon is most effective) and thereafter treating the carbon treated syrup with a strong acid cation exchange resin in the hydrogen form and a weak base anion exchange resin in the free base form.

Glucoamylase is known in the art by many names such as glucamylase, glucogenic enzyme, etc.

Glucoamylase is produced by many types of microorganisms. Certain strains of fungi belonging to the Aspergillus genus such as strains known as *Aspergillus niger* and certain strains of the Rhizopus and Endomyces genus will produce glucoamylase. The above microorganisms also produce enzymes such as alpha-amylase and transglucosidase. The transglucosidase enzymes are capable of producing saccharide polymers which are unfermentable. Thus, the presence of transglucosidase in glucoamylase enzyme preparations is generally considered undesirable.

There are many methods known in the art for preparing glucoamylase. Many methods deal with removing transglucosidase present in glucoamylase enzyme preparations, e.g., the methods disclosed in U.S. Pat. Nos. 2,976,804; 3,042,584; 3,075,886; 3,117,063; and 3,254,003. A significant advance in the art of preparing glucoamylase is disclosed in U.S. Pat. No. 3,012,944 which discloses and claims a process of mutating a microorganism capable of producing glucoamylase. By this method higher yields of glucoamylase and lesser amounts of transglucosidase are produced.

The commercial production of glucoamylase is conducted in a plurality of steps, beginning with a propagation stage initiated by inoculating spores from a slant of a culture into a pre-sterilized nutrient medium usually contained in a shaker flask. The growth is enhanced by aerating the nutrient medium and maintaining the proper pH and temperature therein. The initial stages are referred to as culture development stages. The microorganisms from the last culture development stage (the seed stage) are inoculated into a large scale fermentor to produce commercial quantities of glucoamylase.

The nutrient medium in at least the final stage of development contains as the primary nutrient substances, a carbon source in the form of a carbohydrate and a nitrogen source such as nitrates or proteinaceous materials. As the carbon source, the nutrient medium generally contains ground corn in amounts ranging up to about 10 percent by weight and varying amounts of starch. Prior to inoculating the nutrient medium with the glucoamylase producing microorganism, the nutrient medium is sterilized by heating to a temperature of at least about 120° C. and holding the medium at this temperature for several minutes. Heating the nutrient medium liquefies the ground corn. However, if the solids content of the ground corn is more than 10%, a viscosity build-up occurs such that the agitators in the fermentor are impeded from their normal function. Heating the nutrient medium to the sterilization temperature without the aid of a hydrolytic catalyst such as a liquefying enzyme results in a phenomenon referred to in the art as "steam bumping". Thus, commercial processes for producing glucoamylase employ the use of an alpha-amylase enzyme in the nutrient medium prior to sterilization to assist the liquefaction of the ground corn and to alleviate the problem of "steam bumping".

While the addition of alpha-amylase during the sterilization process aids in the liquefaction of the ground corn, the use of more than 10% by weight of ground corn is generally impractical due to viscosity build-up.

SUMMARY OF THE INVENTION

The present invention provides a process whereby glucoamylase is manufactured in a nutrient medium containing more than about 16% and up to about 25% by weight, dry substance basis of an enzymatically liquefied ground corn. The use of increased levels of liquefied ground corn in the nutrient medium increases the yield of glucoamylase in the fermentation medium.

The invention also provides a process whereby the nutrient medium for preparing glucoamylase containing ground corn is treated with a bacterial alpha-amylase derived from *Bacillus licheniformis* prior to sterilization, whereby the sterilization process liquefies the ground corn in the presence of said enzyme. This embodiment of the invention provides for a reduction of the viscosity in the broth, decreases the power demand from the agitators in the fermenters, allows for the use of higher levels of ground corn (which produces higher levels of glucoamylase) and reduces the time needed to reach the sterilization temperature and thereby requiring less operating attention and reducing the degradation of the nutrient medium constituents.

DETAILED DESCRIPTION OF THE INVENTION

The process of the present invention comprises fermenting a microorganism capable of producing glucoamylase in a nutrient medium containing a nitrogen source and a carbon source wherein said carbon source comprises an enzymatically liquefied ground corn having a solids content greater than about 16% and up to about 25%, dry substance basis.

As another embodiment of the present invention, there is provided a process for the preparation of glucoamylase, comprising: fermenting a microorganism capable of producing glucoamylase in a nutrient medium containing a nitrogen source and a carbon source, wherein the carbon source comprises ground corn which has been liquefied by the action of heat, water and an alpha-amylase enzyme preparation derived from the microorganism *Bacillus licheniformis.*

The process of the invention results in many economic advantages including higher yields in the production of glucoamylase.

One of the more important advantages of the process of the present invention is that it may be carried out in an aqueous medium at relatively high concentrations. The solids content of the ground starch is generally within the range of from about 16% to about 25% although ordinarily the solids content will be in the range of from about 18% to about 22%. Lesser concentrations can be used, and in general as the concentration is decreased, the yield of glucoamylase is also decreased.

The preferred manner of carrying out the process of the invention is to first prepare a culture medium suitable for producing the glucoamylase enzyme preparation. The culture medium is prepared by admixing ground corn as the primary carbon source, corn steep liquor solids as the primary nitrogen source, a bacterial alpha-amylase enzyme preparation, preferably derived from *Bacillus licheniformis,* water and other nutrients such as starch and ammonium salts. This admixture is generally conducted at temperatures ranging from 20° C. to about 60° C. The admixture is then gradually heated by the action of steam to a temperature in the range of from about 110° C. to about 130° C., preferably in the range of from about 120° C. to about 125° C. The bacterial alpha-amylase may be added before or during the steam heating of the nutrient medium. It is preferred, however, to add the enzyme during the heating of the nutrient medium.

The pH of the nutrient medium during the sterilization is adjusted for the maximum efficiency of the bacterial alpha-amylase enzyme preparation. The pH will generally be in the range of from about 4.5 to 7.5, preferably in the range of from about 5.5 to about 6.5 and most preferably from about 5.5 to 6.0.

A preferred manner of conducting the sterilization is to gradually heat the nutrient medium which contains ground corn, corn steep liquor solids, water, and bacterial alpha-amylase to a temperature in the range of from about 55° C. to about 80° C., preferably in the range of from about 65° C. to about 75° C., and at a pH in the range of from about 5.5 to about 6.5. The nutrient medium is preferably held at this temperature for a short period of time, i.e., from about 15 minutes to about 60 minutes, preferably 30 minutes to about 45 minutes to substantially liquefy or thin the ground corn in the medium. Thereafter, the nutrient medium is further heated by the action of steam to a temperature of at least about 110° C., preferably a temperature of at least 120° C. and held at the elevated temperature for a period of at least 30 minutes and preferably at least about 45 minutes. The sterilized nutrient medium is then cooled and the pH is adjusted to about 5.5 to about 6.0.

The sterilized nutrient medium is then inoculated with the glucoamylase producing microorganism. The fermentation is permitted to take place for 48 to 168 hours.

The use of higher quantities of thinned ground corn in the fermentation medium which is facilitated by the use of bacterial alpha-amylase enzyme preparations derived from *Bacillus licheniformis* enables one to obtain in excess of 30 glucoamylase units per ml.

The glucoamylase producing microorganism may be derived from any of the well-known fungal amylase preparations, particularly those derived from members of the Asperigillus genus, the Endomyces genus and the Rhizopus genus. A particularly preferred glucoamylase is that available from the process described in U.S. Pat. No. 3,042,584 whereby a fungal amylase preparation is freed of undesired transglucosidase activity by treatment in an aqueous medium with a clay mineral. Glucoamylase activity units are determined as follows:

The substrate is a 15–18 D.E. acid hydrolysate of corn starch dissolved in water and diluted to 4.0 grams of dry substance per 100 ml. of solution. Exactly 50 ml. of the solution is pipetted into a 100 ml. volumetric flask. To the flask is added 5.0 ml. of 1.0 molar sodium acetate-acetic acid buffer (pH: 4.3). The flask is placed in a water bath at 60° C. and after 10 minutes the proper amount of enzyme preparation is added. At exactly 120 minutes after addition of the enzyme preparation the solution is adjusted to a phenolphthalein endpoint with one normal sodium hydroxide. The solution is then cooled to room temperature, and diluted to volume. A reducing sugar value, calculated as dextrose, is determined on the diluted sample and on a control with no enzyme preparation added. Glucoamylase activity is calculated as follows:

$$A = \frac{S - B}{2 \times e}$$

where

A = glucoamylase activity units per ml. (or per gram) of enzyme preparation.
S = reducing sugars in enzyme converted sample, grams per 100 ml.
B = reducing sugars in control, grams per 100 ml.
E = amount of enzyme preparation used, ml. (or grams).
"S" should not exceed 1.0 grams per 100 ml.

The bacterial alpha-amylase used to thin the ground corn preferably is one which is active at a relatively low pH, i.e., within the range of from about 5.0 to about 8.0, and also at relatively high temperatures, i.e., up to about 105° C. Preferred sources of such alpha-amylases include certain species of the Bacillus microorganism, viz., Bacillus licheniformis. Suitable alpha-amylases are described in Austrian patent application No. 4836/70, British Pat. No. 1,296,839 and in U.S. Pat. No. 3,697,378. Especially suitable amylases are those derived from B. licheniformis as described in the above Austrian patent application and British patent. Particularly preferred is that alpha-amylase derived from B. licheniformis strain NCIB 8061; other specific microorganisms include B. licheniformis strains NCIB 8059; ATCC 6598, ATCC 6634, ATCC 8480, ATCC 9945A and ATCC 11945. They are unusually effective in the liquefaction of ground corn. One such is identified by the trade name "THERMAMYL", available from Novo Terapeutisk Laboratorium, Copenhagen, Denmark. For such use it should be used in a concentration ranging from about 1.0 to about 25 units per gram of ground corn (dry basis) under conditions of pH and temperature set out earlier herein. THERMAMYL is characterized by the following properties:

(a) it is thermally stable;
(b) it has a broad range of pH activity; and
(c) its activity and heat stability are independent of the presence of added calcium ion.

Its analysis is as follows:

| | |
|---|---|
| Dry Substance, % | 94.6 |
| Alpha-amylase activity, U/g (as is) | 9,124 |
| Protein % d.b. | 21.2 |
| Ash, % d.b. | 64.4 |
| Calcium, % d.b. | 4.9 |

Other suitable alpha-amylases include THERMAMYL 60 (a liquid) and THERMAMYL 120 (a solid) having the following analyses:

| | THERMAMYL 60 | THERMAMYL 120 |
|---|---|---|
| Dry Substance, % | 35.4 | 98.8 |
| Alpha-Amylase activity, U/g (as is) | 1,156 | 2,105 |
| Protein, % d.b. | 26.5 | 21.2 |
| Ash, % d.b. | 60.1 | 91.2 |
| Calcium, % d.b. | 0.04 | 0.72 |

-continued

| | THERMAMYL 60 | THERMAMYL 120 |
|---|---|---|
| Sodium, % d.b. | 12.3 | 12.2 |

The alpha-amylase activity of an enzyme is determined as follows:

The enzyme is allowed to react with a standard starch solution under controlled conditions. Enzyme activity is determined by the extent of starch hydrolysis, as reflected by a decrease in iodine-staining capacity, which is measured spectrophotometrically. The unit of bacterial alpha-amylase activity is the amount of enzyme required to hydrolyze 10 mg. of starch per minute under the conditions of the procedure. The method is applicable to bacterial alpha-amylases, including industrial preparations, except materials which possess significant saccharifying activity.

From 0.3 to 0.5 gram of solid sample or from 0.3 to 1.0 ml. of a liquid sample is dissolved in a sufficient quantity of 0.0025 M aqueous calcium chloride to give an enzyme solution containing approximately 0.24 unit of activity per ml.

A mixture of 10 ml. of 1% Lintner starch solution, equilibrated to 60° C., and 1 ml. of the enzyme sample to be tested is mixed and held in a 60° C. constant temperature bath for exactly 10 minutes. A 1-ml. sample is removed and added to a mixture of 1 ml. of 1 M aqueous hydrochloric acid and about 50 ml. of distilled water. The iodine-staining capacity of such acidified sample then is determined by adding 3.0 ml. of 0.005% aqueous iodine solution, diluting to 100 ml. with distilled water, and mixing well. The absorbance of the solution, relative to that of distilled water, is measured at 620 nm, in a 2-cm cell. A similar measurement is made of the standard starch solution (to which water is added instead of the enzyme solution) to provide a blank adsorbance.

The enzyme activity, in units/gram or/ml. is equal to $$\frac{(\text{Blank Absorbance} - \text{Sample Adsorbance}) \times \text{Dilution Factor} \times 50}{\text{Blank Adsorbance} \times 10 \times 10}$$

The term "D.E." and dextrose equivalent value used herein refer to the reducing sugars content of the dissolved solids in a starch hydrolysate expressed as percent dextrose as measured by the Schoorl method (*Encyclopedia of Industrial Chemical Analysis*, Vol. 11, pp. 41–42).

The invention is further illustrated by the following examples which, however, are not to be taken as limiting in any respect. All parts and percentages, unless expressly stated to be otherwise, are by weight.

EXAMPLE 1

(a) Culture and Seed Development

The following procedure was employed to prepare the inoculum for producing glucoamylase.

A loop of spores from a sporulated slant of a mutant of Aspergillus niger strain (as in U.S. Pat. No. 3,012,944 to Armbruster) was transferred to a 1 liter Erlenmeyer flask containing 200 ml. of sterile medium of the following composition:

| | |
|---|---|
| Corn steep liquor solids | 2.0% d.b. |
| Ground yellow corn | 5.0% d.b. |

The inoculated flask was incubated for 48 hours at 30° C. to 35° C. on a rotary shaker. The contents of the flask were then transferred into a 7.5 liter fermentor containing 4 liters of the same presterilized seed medium (sterilized for 1.5 hours at 121° C., pH 6.0). The 7.5 liter seed fermentor was then stirred at 500 revolutions per minute with air injection at 3 liters per minute and at a temperature of 33° C. for 24 hours. The inoculum thus produced was used in 40-liter fermentors for production of glucoamylase.

(b) Production of Sterilized Nutrient Medium

The sterilized Nutrient Medium to be used for glucoamylase production of this example was produced in several separated batches, each in 40-liter fermentors having respectively a six bladed impeller means of 4.5" diameter and a width of ⅞" and a sterile air source of 24 liters per minute. The fermentors were operated at 600 revolutions per minute, 15 p.s.i.g., vessel pressure and at a temperature of about 33° C. The fermentors were each charged with 29 liters of fermentation medium having the following composition:

| | |
|---|---|
| Ground No. 2 Corn (Fermentors 1, 2 and 3) or | 15.9% d.b., 4770 g.,d.b. 5450 g., as is |
| Ground No. 2 Corn Fermentors (No. 4) | 20.0% d.b., 6000 g.,d.b., 6900 g., as is |
| Corn Steep Liquor Solids | 2.5% d.b. 750 g.,d.b. 150 g., as is |
| Sodium Hydroxide to pH (prior to sterilization) | 6.0–6.5 |

Alpha-amylase (thermanyl 60) was added to the fermentation medium at levels of 1.6, 2.8 and 4.0 CPC alpha-amylase units per gram of ground corn, d.b., respectively. CPR-8 alpha-amylase was added to the fourth fermentor at the rate of 1.6 units per gram of ground corn, d.b. The enzyme was added during the heat-up (with steam) of the fermentor as the temperatures passed 60° C. The temperature was held at 75° C. for 30 minutes, then allowed to rise to 121° C. for a 45-minute sterilization period. After sterilization, the volume in the fermentors was 30 liters.

The different bacterial alpha-amylase enzyme preparations, used to liquefy the ground corn in the fermentors during the liquefaction and sterilization of the nutrient medium, were Thermamyl 60 liquid, having a potency of 1270 CPC alpha-amylase units/ml. (a bacterial alpha-amylase enzyme preparation derived from Bacillus licheniformis), and CPR-8, a dry preparation on a calcium carrier having a potency of 3200 CPC alpha-amylase units/gram. (CPR-8 is manufactured and sold by the Wallerstein Division of Baxter Laboratories, Inc.).

Viscosity measurements were made from the above-described nutrient media after both thinning and sterilization to ascertain the benefits of using enzymes derived from Bacillus licheniformis. The thinning and sterilization were conducted in the above-described 40-liter fermentor. The nutrient medium (containing 15.9%, d.b. ground corn) was steam heated to 75° C. at a pH of 6.0. The alpha-amylase was added as the temperature passed 60° C. The temperature was held at 75° C. for 30 minutes at thereafter sterilized for 45 minutes at 121° C.

The viscosity measurements of the resulting nutrient mediums are set forth in Table I.

TABLE I

| Effect of Enzyme Thinning On Post-Sterile Viscosity | | | | |
|---|---|---|---|---|
| | Alpha Amylase (units/g. corn d.b.) | | | |
| | Thermamyl 60 | | | CPR. 8 |
| | 1.6 | 2.8 | 4.0 | 1.6 |
| Brookfield Viscosity, c.p.[a] | 155 | 170 | 155 | 3600 |

[a] measured at 33° C.

The above data clearly demonstrates the superior liquefaction and thinning obtained using an alpha-amylase derived from Bacillus licheniformis. This unique advantage (lower viscosity in the fermentation medium) results in better heat transfer (facilitates sterilization), reduced power consumption from the agitators, and reduced steam "bumping" due to steam injection into ground corn medium during heating as the starch is liquefied (Heat-up was smooth with the use of Thermamyl, whereas the fermentors "rocked" during heat-up with CPR-8). The more effective liquefaction using Thermamyl permits faster heat-ups to sterilization temperature and faster cool downs which means that the sterilization cycle can be shortened to thereby increase fermentor productivity.

In another series of experiments in the 40-liter fermentor containing 15.9% d.b. ground corn, 3–12 CPC alpha-amylase units per gram of corn, d.b. of CPR-8 enzyme were added in the same manner previously described during sterilization at a pH of 6.0. In each instance a heavy gelled mass was produced. When using Thermamyl in comparable experiments the corn medium became visually thin at both 15.9% or 20% d.b. levels.

(c) Glucoamylase Fermentation.

Several glucoamylase fermentations were conducted in the 40-liter fermentor using nutrient mediums containing 15.9% and 20.0% d.b. liquefied and sterilized ground corn. At the 20.0% d.b. corn level, both CPR-8 and Thermamyl were used for comparison. The sterilized nutrient medium had a volume of 30 liters. Each batch was charged with 1.5 liters of the inoculum prepared as in Example 1 (a) to bring the operating volume to 31.5 liters. The ground corn in all of the nutrient mediums was liquefied with 1.6 CPC units of alpha-amylase per gram of corn, d.b. The glucoamylase fermentations were run for periods up to 168 hours. Samples were periodically withdrawn for analysis. The yield of glucoamylase using 15.9% d.b. corn (CPR-8 liquefied) after 144 hours was about 29 units per ml. compared to 32 units per ml. using 20.0% corn d.b. liquefied with CPR-8 at 144 hours of fermentation. The yield of glucoamylase using 20.0% d.b. corn liquefied with Thermamyl was 37 units per ml. at 144 hours. These tests clearly demonstrate that higher yields of glucoamylase can be achieved by using more than 16% d.b. liquefied ground corn in the medium regardless of the alpha-amylase used and still higher yields of glucoamylase are obtained when using ground corn liquefied with an alpha-amylase derived from Bacillus licheniformis.

An additional ten (10) batches were conducted in the 40-liter fermentor using 20% d.b. ground corn in the nutrient medium, five (5) each using the CPR-8 enzyme and Thermamyl 60 liquid. The batches were conducted in the same manner described above using 1.5 liters of the inoculum prepared as in 1 (a). The results of the tests are set forth in Table II.

nutrient medium suitable for fermentation by the use of ground corn liquefied by the action of a bacterial alpha-amylase enzyme preparation derived from *Bacillus licheniformis*. This improved process for preparing a

TABLE II

40-LITER GLUCOAMYLASE FERMENTATIONS

Results of 20% d.b. Corn, 2.5% d.b. Cornsteep Batches using CPR-8 or Thermamyl Alpha-Amylase for Thinning

| Batch | Peak GA µ/ml | Peak Alpha Holo, µ/ml | Alpha Ratio H/GA | Unit TG/Unit GA | Age, Hours |
|---|---|---|---|---|---|
| *Batches Thinned with CPR-8 Alpha-Amylase, 1.6 Units per Gram Corn d.b.* | | | | | |
| A | 35.0 | 78.8 | 2.25 | — | 163 |
| B | 35.8 | 80.5 | 2.25 | .91 | 168 |
| C | 37.0 | 67.0 | 1.81 | — | 168 |
| D | 31.8 | 52.3 | 1.65 | 1.25 | 168 |
| E | 34.6 | 66.7 | 1.93 | 1.12 | 162 |
| Average | 34.8 | 69.1 | 1.98 | 1.09 | 165 |

| Batch | Peak GA µ/ml | Peak Alpha Holo, µ/ml | Alpha Ratio H/GA | Unit TG/Unit GA | Age, Hours | Units Alpha-Amylase-per g Corn d.b. |
|---|---|---|---|---|---|---|
| *Batches Thinned with Thermamyl Alpha-Amylase* | | | | | | |
| F | 33.2 | 70.5 | 2.12 | .91 | 168 | 4.0 |
| G | 36.6 | 65.7 | 1.79 | .95 | 140 | 1.6 |
| H | 33.0 | 69.0 | 1.95 | .92 | 162 | 1.6 |
| I | 36.5 | 71.2 | 2.24 | 1.00 | 162 | 2.8 |
| J | 34.4 | 77.0 | 1.93 | 1.12 | 162 | 4.0 |
| Average | 34.8 | 70.7 | 2.00 | .98 | 159 | |
| Averages for 15.9% Corn 27.5 Medium | | 54.2 | 2.01 | Not Determined | 146 | |

The results in Table II describe the averages for each group of five (5) batches as 34.8 glucoamylase units per ml. No significant variations were noted in the alpha-holoamylase/glucoamylase ratio or in the transglucosidase/glucoamylase ratio. The results also demonstrate a 27% increase in glucoamylase level in the filtered broth regardless of the liquefaction enzyme used. However, the use of Thermamyl improves the overall economy of the process due to reduced viscosities as described above.

EXAMPLE 2

This example demonstrates the improved results in using an alpha-amylase derived from *Bacillus licheniformis* (Thermamyl 60 liquid) compared with CPR-8 in preparing a glucoamylase nutrient medium in a plant fermentor. A 20,000 gallon plant fermentor was charged with the following compositions in two (2) separate comparative experiments.

TABLE III

| Nuturient Medium | CPR-8 | Alpha-Amylase Thermamyl 60 |
|---|---|---|
| Water | 12,000 Gallons | 12,000 Gallons |
| Steepwater at 52-54% d.s. | 754 Gallons | 754 Gallons |
| Ground Corn at 15% H₂O | 28,000 Pounds | 28,000 Pounds(b) |
| CPR-8 | 13 Pounds(a) | — |
| Thermamyl 60 Liquid | — | 42.5 Pounds |
| Time To Reach 250° F. | 8 hours(c) | 1.5 hours |
| Time to Cool down | 3 hours | 1.5 hours |

(a)Equivalent to 1.6 CPC alpha-amylase units/gram corn, d.b.
(b)28,000 pounds is the maximum level feasible when using CPR-8, however as much as 35,000 pounds of ground corn can be used with Thermamyl which in turn results in higher yields of glucoamylase.
(c)Eight (8) hours is required when using CPR-8 because one must allow the contents to heat to 180° F. using only friction from agitators before addition of CPR-8 because of the limited range of stability. Then steam must be added very slowly to prevent violet shaking of the fermentors. None of these precautions are needed when using Thermamyl.

GENERAL

As seen from the above data, the process of the invention provides an improved method of manufacturing a nutrient medium is suitable for most any fermentation which requires starch as a carbon source. By the use of the *Bacillus licheniformis* bacterial alpha-amylase thinned ground corn the overall economics of the fermentation are improved, especially in the case of preparing glucoamylase.

The glucoamylase enzyme preparation prepared by the process of the invention can be used in the hydrolysis of starch to prepare dextrose and/or dextrose-containing syrups. A suitable process involves partially hydrolyzing starch with acid or enzyme and thereafter converting the partially hydrolyzed starch with the glucoamylase to the desired level of conversion. The partially hydrolyzed starch is preferably substantially liquefied by the action of a bacterial alpha-amylase enzyme preparation to a D.E. not substantially above about 20. A preferred process for preparing the partially hydrolyzed starch is disclosed in U.S. Ser. No. 107,436, U.S. Pat. No. 3,853,706, the disclosure of which is incorporated herein by reference. Another preferred process for preparing the partially hydrolyzed starch to be used in conjunction with the glucoamylase preparation of the invention is disclosed in U.S. Ser. Nos. 437,452, 437,101, 437,264, and 452,154, now U.S. Pat. Nos. 3,922,199; 3,922,197; 3,922,198 and 3,922,200, respectively, granted Nov. 25, 1975 the disclosures of which are incorporated herein by reference.

While the invention has been described in connection with specific embodiments thereof, it will be understood that it is capable of further modification, and this application is intended to cover any variations, uses, or adaptions of the invention following, in general, the principles of the invention and including such departures from the present disclosure as come within known or customary practice in the art to which the invention pertains and as may be applied to the essential features hereinbefore set forth, as fall within the scope of the invention.

We claim:

1. In a process for the production of glucoamylase comprising, cultivating a culture of a glucoamylase-producing microorganism in a pre-sterilized nutrient medium under aeration in a plurality of development stages and thereafter inoculating, in a final development stage, the last culture development stage (seed stage) of glucoamylase-producing microorganisms in a pre-sterilized fermentation medium comprising a carbon source in the form of carbohydrates and a nitrogen source, wherein the carbon source comprises enzymatically liquified ground corn, and fermenting the innoculated pre-sterilized fermentation medium to thereby obtain the glucoamylase enzyme, the improvement comprising:

preparing the sterilized fermentation medium by the steps comprising:
(1) forming a fermentation medium by admixing ground corn as a primary carbon source, a primary nitrogen source and water at a temperature ranging from about 20° C. to about 60° C.;
(2) heating the medium in step (1) by the action of steam to a temperature in the range from about 55° C. to about 80° C. and at a pH in the range from about 4.5 to about 7.5 in the presence of a bacterial alpha-amylase preparation derived from a *Bacillus licheniformis* microorganism, said bacterial alpha-amylase enzyme preparation being added to the medium before or during the steam heating of the medium for a time sufficient to substantially liquify all the ground corn
(3) further heating the medium by the action of steam at a temperature of at least 100° C. and holding the medium at this temperature to sterilize the medium; and
(4) cooling the medium to thereby obtain a sterilized fermentation medium containing enzymatically liquified ground corn having a solids content greater than about 16% and up to about 25% by weight dry substance basis which is inoculated with the development stage (seed stage) of glucoamylase-producing microorganism to produce glucoamylase by fermentation in said medium.

2. The process in accordance with claim 1, wherein enzymatically liquefied ground corn has a solids content in the range from about 18% to about 22%, dry substance basis.

3. The process in accordance with claim 1, wherein the enzymatically liquefied ground corn has a solids content of about 20%, dry substance basis.

4. The process in accordance with claim 1, wherein said bacterial alpha-amylase enzyme preparation is derived from a microorganism selected from the group consisting of *Bacillus licheniformis* NCIB 8061, NCIB 8059, ATCC No. 6598, ATCC No. 6634, ATCC No. 8480, ATCC No. 9945a and ATCC No. 11945.

5. The process in accordance with claim 1, wherein said glucoamylase-producing microorganism is derived from *Aspergillus niger*.

6. The process in accordance with claim 5, wherein said microorganism is a mutant strain.

7. The process in accordance with claim 1, wherein the fermentation is conducted at a pH in the range from about 3.5 to about 6.0.

8. The process of claim 1, wherein the primary nitrogen source comprises corn steep liquor solids.

* * * * *

UNITED STATES PATENT AND TRADEMARK OFFICE
CERTIFICATE OF CORRECTION

PATENT NO. : 4,169,013
DATED : September 25, 1979
INVENTOR(S) : Jay A. Smith, Jeffrey R. Frankiewicz It is certified that error appears in the above-identified patent and that said Letters Patent are hereby corrected as shown below:

In the Abstract, line 5, change "alpha-amylase" to --alpha-amylase--.
In the Abstract, line 6, change "alpha-amylase" to --alpha-amylase--.
Col. 1, line 44, change "alpha-amylase" to --alpha-amylase--.
Col. 1, line 51, change "alpha-amylase" to --alpha-amylase--.
Col. 1, line 56, change "alpha-amylase" to --alpha-amylase--.
Col. 1, line 62, change "alpha-amylase" to --alpha-amylase-- and "alpha" to --alpha---.
Col. 2, line 20, change "Asper-" to --Asper---.
Col. 2, line 21, change "gillus" to --gillus--.
Col. 2, line 22, change "Rhizopus" to --Rhizopus--, and "Endomyces" to --Endomyces--.
Col. 2, line 24, change "alpha-amylase" to --alpha-amylase--.
Col. 3, line 5, change "alpha-amylase" to --alpha-amylase--.
Col. 3, line 8, change "alpha-amylase" to --alpha-amylase--.
Col. 3, line 23, change "alpha-amylase" to --alpha-amylase--.

Col. 3, line 52, change "alpha-amylase" to --alpha-amylase--.
Col. 4, line 4, change "alpha-amylase" to --alpha-amylase--.
Col. 4, line 12, change "alpha-amylase" to --alpha-amylase--.
Col. 4, line 18, change "alpha-amylase" to --alpha-amylase--.
Col. 4, line 25, change "alpha-amylase" to --alpha-amylase--.
Col. 4, line 46, change "alpha-amylase" to --alpha-amylase--.

UNITED STATES PATENT AND TRADEMARK OFFICE
CERTIFICATE OF CORRECTION

PATENT NO. : 4,169,013
DATED : September 25, 1979
INVENTOR(S) : Jay A. Smith, Jeffrey R. Frankiewicz It is certified that error appears in the above-identified patent and that said Letters Patent are hereby corrected as shown below:

Col. 4, line 52, change "Aspergillus" to --*Aspergillus*-- and "Endomyces" to --*Endomyces*--.
Col. 4, line 53, change "Rhizopus" to --*Rhizopus*--.
Col. 5, line 20, change "alpha-amylase" to --*alpha*-amylase--.
Col. 5, line 25, change "Bacillus" to --*Bacillus*--.
Col. 5, line 26, change "Bacillus licheniformis" to --*Bacillus licheniformis*-- and "alpha-amylases" to --*alpha*-amylases--.
Col. 5, line 32, change "alpha-amylase" to --*alpha*-amylase--.
Col. 6, line 22, change "M" to --$\bar{M}$--.
Col. 6, line 29, change "M" to --$\bar{M}$--.
Col. 6, line 32, change "0.005%" to --0.05%--.
Col. 7, line 37, change "Alpha-amylase" to --*alpha*-Amylase--.
Col. 7, line 37, change "thermamyl 60" to --Thermamyl 60--.
Col. 7, line 39, change "alpha-amylase" to --*alpha*-amylase--.

UNITED STATES PATENT AND TRADEMARK OFFICE
CERTIFICATE OF CORRECTION

PATENT NO. : 4,169,013
DATED : September 25, 1979
INVENTOR(S) : Jay A. Smith, Jeffrey R. Frankiewicz It is certified that error appears in the above-identified patent and that said Letters Patent are hereby corrected as shown below:

Col. 7, line 38, after "medium" add --in each of three fermentors--.
Col. 7, line 43, change "fermentor" to --fermentors--.
Col. 7, line 48, change "alpha-amylase" to --*alpha*-amylase--.
Col. 7, line 52, change "alpha-amylase" to --*alpha*-amylase--.
Col. 7, line 53, change "alpha-amylase" to --*alpha*-amylase-- and "Bacil" to --*Bacil*---.
Col. 7, line 54, change "lus lichenformis" to --*lus lichenformis*--.
Col. 7, line 55, change "alpha-" to --*alpha*---.
Col. 7, line 66, change "alpha-amylase" to --*alpha*-amylase--.

Col. 8, line 6, change "Alpha Amylase" to --*alpha*-Amylase--.
Col. 8, line 14, change "alpha-amy-" to --*alpha*-amy---.

Col. 8, line 30, change "alpha-amylase" to --*alpha*-amylase--.
Col. 8, line 48, change "alpha-" to --*alpha*---.
Col. 8, line 62, change "alpha-amylase" to *alpha*-amylase--.
Col. 8, line 64, change "alpha-amylase" to *alpha*-amylase--.
Col. 9, line 7, change "Alpha-Amylase" to --*alpha*-Amylase--.
Col. 9, line 11, change "Alpha-Amylase" to --*alpha*-Amylase--.
Col. 9, line 18, change "Alpha-Amylase" to --*alpha*-Amylase--.
Col. 9, line 19, change "Alpha-Amylase" to --*alpha*-Amylase--.
Col. 9, line 31, change "alpha-" to --*alpha*---.
Col. 9, line 42, change "alpha-amylase" to --*alpha*-amylase--.

UNITED STATES PATENT AND TRADEMARK OFFICE
CERTIFICATE OF CORRECTION

PATENT NO. : 4,169,013

DATED : September 25, 1979

INVENTOR(S) : Jay A. Smith, Jeffrey R. Frankiewicz

It is certified that error appears in the above-identified patent and that said Letters Patent are hereby corrected as shown below:

```
Col. 9, line 49, change "Alpha-Amylase" to --alpha-Amylase--.
Col. 9, line 58, change "alpha-amylase" to --alpha-amylase--.
Col. 9, line 63, change "violet" to --violent--.
Col. 10, line 2, change "alpha-" to --alpha---.
Col. 10, line 32, change "alpha-amylase" to --alpha-amylase--.
Col. 10, line 44, change "alpha-amylase" to --alpha-amylase--.

Col. 11, line 26, change "alpha-amylase" to --alpha-amylase--.
Col. 11, line 27, change "alpha-" to --alpha---.
Col. 11, line 31, after "ground corn" add --;--.
```

Signed and Sealed this

Eighth Day of April 1980

[SEAL]

Attest:

SIDNEY A. DIAMOND

Attesting Officer

Commissioner of Patents and Trademarks